United States Patent [19]

Yamauchi

[11] Patent Number: 4,512,865
[45] Date of Patent: Apr. 23, 1985

[54] ELECTROLYTIC STERILIZER FOR CONTACT LENSES

[75] Inventor: Masakatu Yamauchi, Kani, Japan

[73] Assignees: Tanica Electric Co., Ltd., Tajimi; Tomei Sangyo Kabushiki Kaisha, Nagoya, both of Japan

[21] Appl. No.: 617,815

[22] Filed: Jun. 6, 1984

[51] Int. Cl.³ .............................................. C25B 9/00
[52] U.S. Cl. ................................... 204/271; 204/275
[58] Field of Search ....................... 204/242, 275, 271

[56] References Cited

U.S. PATENT DOCUMENTS 4,202,740  5/1980  Stoner et al. ................ 204/271
4,289,599  9/1981  Fushihara ..................... 204/271
4,316,787  2/1982  Themy .......................... 204/271

Primary Examiner—R. L. Andrews
Attorney, Agent, or Firm—Oblon, Fisher, Spivak, McClelland & Maier

[57] ABSTRACT

An electrolytic sterilizer for contact lenses comprising a main body accommodating a power source unit and a sterilizing container detachably mountable on the main body and having electrodes electrically connectable, through container-side contacts and main body-side contacts, to said power source for electrolysis, wherein the main body has a groove for a waste solution, and the main body-side contacts are located outside of the groove.

2 Claims, 3 Drawing Figures

ELECTROLYTIC STERILIZER FOR CONTACT LENSES

BACKGROUND OF THE INVENTION

1. Field of the Invention

The present invention relates to an electrolytic sterilizer for contact lenses comprising a main body accommodating a power source unit and a sterilizing container detachably mountable on the main body. More particularly, the present invention relates to a specific structure for the electrode connection in such an electrolytic sterilizer.

2. Description of the Prior Art

Conventional hydrated contact lenses composed principally of a hydrophilic monomer such as 2-hydroxyethyl methacrylate normally contain more than about 30% by weight of water. As a result, the hydrated contact lenses are likely to provide by themselves a favorable environment for the multiplication of various detrimental bacteria. Furthermore, it is very dangerous to wear bacteria-infected contact lenses on the eyes without treating them in any way, since this practice may lead to serious damage to the eye tissue. For this reason, it is essential to sterilize such hydrated contact lenses periodically.

For example, the most common method for sterilizing the hydrated contact lenses is a method wherein the lenses are boiled for a predetermined time. This method is extremely effective for sterilizing the lenses, but at the same time it has the following serious disadvantages, which may be regarded as fatal defects:

(1) The protein and other components in tears deposited on the lens undergo a thermal metamorphosis due to the boiling operation and stick to the lens surface, thereby impairing the optical properties of the lens and remarkably reducing the comfortableness of wearing the lens on the eye.

(2) The sparingly cross-linked hydrophilic polymer, which is the material of hydrated contact lenses, is likely to deteriorate due to repeated severe boiling treatments. Thus, the lens is subject to discoloration and/or change in standard configuration, thereby resulting in reduced useful life of the lens.

(3) Boiling sterilization may not be accomplished on non-hydrated contact lenses which are composed of polymethyl methacrylate and/or silicone rubber.

In order to alleviate the drawbacks associated with boiling sterilization, it has been proposed to employ a method wherein the contact lenses are sterilized by various disinfectant fluids such as solutions containing, e.g., thimerosal or chlorohexadine. In such a treatment, the disinfectant component will readily be adsorbed into the lens body because of the large structural spaces between molecules constituting the hydrated contact lenses. However, the adsorbed disinfectant component has the potential danger of causing hypersensitive inflammation to the eye tissue.

There has also been proposed a method wherein the lenses are sterilized with a 3% aqueous solution of hydrogen peroxide, and then the solution is contacted with a catalyst such as platinum to decompose and detoxicate the hydrogen peroxide into water and oxygen. This method also has disadvantages in that it requires a considerably longer time in sterilization and is impractical because of its complicated operation.

Further, Japanese Unexamined Patent Publication No. 68454/1981 discloses a method wherein contact lenses kept in a container filled with a physiological sodium chloride solution are sterilized and disinfected as they are kept in the container. The sterilization and disinfection is accomplished by electrolyzing the physiological sodium chloride solution to form an effective amount of sodium hypochlorite as a disinfectant. An electrolytic sterilizer for contact lenses of this type comprises a main body accommodating a power source unit, a sterilizing container detachably mountable on the main body, and a structure for electric connection, which is provided at the joint portion. The structure for electric connection in this type of sterilizer comprises base body-side contacts formed of a material such as conductive rubber in a recess of the main body designed to receive the sterilizing container. If the physiological sodium chloride solution to be used for sterilization or the sodium hypochlorite solution obtained by the electrolysis is deposited or dropped in a small amount and if the sterilizing container is connected for sterilization, electrolysis takes place between the body side contacts, whereby the electrolysis in the sterilizing container will be disturbed or impaired and a disinfectant solution having an adequate concentration will not be formed. Accordingly, if the contact lenses are washed and sterilized with such a disinfectant solution, no adequate effectiveness will be obtained, and if such contact lenses still infected with bacteria are worn, there will be a possible danger of hurting the eyes. Further, there is an additional drawback that the contacts are likely to wear out as a result of the electrolysis which takes place between the contacts on the main body side.

SUMMARY OF THE INVENTION

It is an object of the present invention to provide an electrolytic sterilizer for contact lenses which is capable of minimizing the above-mentioned difficulties.

Namely, the present invention provides an electrolytic sterilizer for contact lenses comprising a main body accommodating a power source unit and a sterilizing container detachably mountable on the main body. The power source unit and the sterilizing container are electrically connectable through container-side contacts and main body-side contacts. The main body has a groove for waste solution, and the main body-side contacts are located outside of the groove.

Now, the present invention will be described in detail with reference to the preferred embodiments as illustrated in the accompanying drawings.

DETAILED DESCRIPTION OF THE PREFERRED EMBODIMENTS

Figure 1:
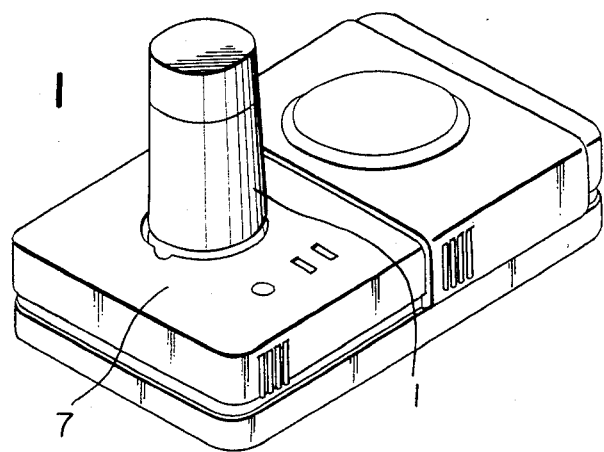
FIG. 1 is a perspective view of an electrolytic sterilizer according to the present invention, illustrating the entire outer appearance thereof.
Figure 2:
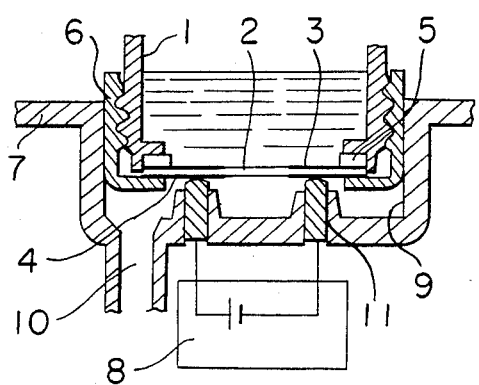
FIG. 2 is a cross sectional view of the essential portion of the structure for electric connection for the electrodes in the electrolytic sterilizer of FIG. 1.

Referring to the drawings, reference numeral 1 designates a sterilizing container made of a synthetic resin, and numeral 2 designates an electrode unit for conducting an electric current in the sterilizing container 1. The electrode unit 2 comprises electrolytic electrodes 3 formed of a highly ionizable element such as platinum or gold on the upper surface of a ceramic base plate and sterilizing container-side contacts 4 fixed on the lower surface of the base plate. The respective electrodes 3 and contacts 4 are electrically connected along the respective sides of the base plate or through through-holes provided in the base plate. The electrode unit 2 is fixed on the bottom of the sterilizing container 1 by an outer cover 6 with a packing 5 interposed inbetween the sterilizing container 1 and the outer cover 6.

Reference numeral 7 is a main body accommodating a power source unit 8 which internally contains a battery. Reference numeral 9 is a groove for waste solution provided at the bottom of the recess of the base body designed to receive the sterilizing container 1. The groove 9 for the waste solution is provided with a discharge outlet 10. The sterilizing container 1 having the electrode unit 2 fixed by the outer cover 6, is detachably fitted in a recess in the main body 7 for each use.

Reference numeral 11 designates a pair of contacts on the main body 7. The cores of the contacts 7 are made of, e.g., rubber in a conductive cylindrical shape, and their peripheries are supported by an electrically insulative support portion protruded from the waste solution groove 9 of the main body 7. Thus, the main body-side contacts 11 are readily electrically connectable with the sterilizing container-side contacts 4 whenever the sterilizing container 1 is fitted in the recess of the main body 7 for use, but the electrically insulative support portions prevent electrolysis from occurring in waste sterilizer solution accidentally spilled into the recess in the main body 7.

Figure 3:
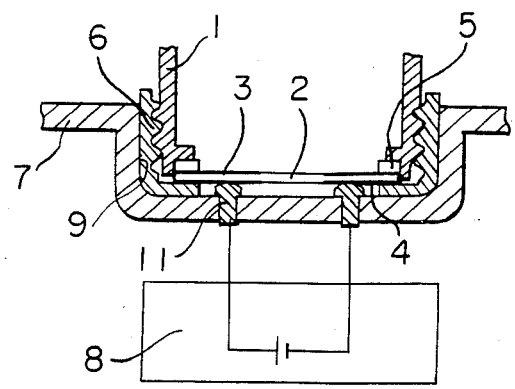
FIG. 3 is a vertical cross sectional view illustrating a conventional structure for the electric connection for the electrodes in a prior art sterilizer.

In a prior art separable type electrolytic sterilizer for contact lenses such as is shown in FIG. 3, it is common that, as the attaching and detaching of the sterilizing container 1 to and from the main body 7 are repeated every time the sterilizer is used, the disinfectant solution leaks from the sterilizing container 1 and deposits on the contacts 11 of the main body 7. Moreover, the disinfectant solution deposited on the contacts 11 tends to cause undesirable electrolysis outside the sterilizing container 1.

In contrast, in the separable type electrolytic sterilizer for contact lenses according to the present invention, the electrically insulative protrusions are provided at the bottom of the recess in the main body 7, and the main body-side contacts 11 are provided on the protrusion. Moreover, a groove 9 for a waste solution and a discharge outlet 10 are provided at the bottom of the recess of the main body 7. The contacts 11 are located outside the waste solution groove 9, and the above-mentioned undesirable electrolysis is unlikely to take place. Further, no foreign matter is permitted to interfere with the electric connection. Accordingly, no disturbance of the electric current is likely to take place.

Further, it is also possible to sterilize the physiological sodium chloride solution for preserving contact lenses, by filling a bottle capped with the outer cover 6 having the electrode unit 2, with the sodium chloride solution, and fitting the bottle in the main body 7, whereby the electrolytic sterilization is conducted by sodium hypochloride generated in the solution.

As is evident from the foregoing description of the construction and the manner of the operation, the present invention has the following advantages.

Namely, in the present invention, the main body-side contacts are provided outside the waste solution groove—i.e., on electrically insulated supports protruded from the waste solution groove. Therefore, even if a washing solution or a physiological sodium chloride solution is dropped between the contacts, it will be possible to avoid deposition of such solution between the tops of the main body-side contacts and the contacts of the electrode unit, whereby a stabilized electrolytic sterilization can be conducted. Further, in the present invention, the washing solution, or a physiological sodium chloride solution dropped into the waste solution groove is discharged from the discharge outlet provided at the bottom of the groove, whereby the washing can readily be conducted and it is possible to avoid the deposition of foreign matter or stains.

What is claimed is:

1. An electrolytic sterilizer for contact lenses, said sterilizer comprising:
   (a) a main body accomodating a power source unit, said main body having a recess in the upper surface thereof;
   (b) a pair of protrusions made of an electrically insulating material protruding upwardly from the bottom of said recess, said pair of protrusions defining a groove in the bottom of said recess which receives waste sterilizer solution accidentally spilled into said recess in said main body;
   (c) a sterilizer container detachably mountable in said recess in said main body;
   (d) a pair of electrolytic electrodes for conducting an electric current in said sterilizer container;
   (e) a pair of sterilizing container contacts in electrical contact with said pair of electrolytic electrodes; and
   (f) a pair of main body contacts in electrical contact with said power source unit, said pair of main body contacts being mounted in and protruding upwardly from said pair of protrusions and being positioned to make electrical contact with said pair of sterilizer container contacts when said sterilizer container is mounted in said recess in said main body, whereby:
   (g) the portions of said pair of main body contacts which come into contact with said pair of sterilizer container contacts are normally above the level of waste sterilizer solution accidentally spilled into said recess in said main body and
   (h) said pair of protrusions made from an electrically insulating material normally prevent electrolysis from occurring in waste sterilizer solution accidentally spilled into said recess in said main body.

2. An electrolytic sterilizer for contact lenses as recited in claim 1 wherein said groove has a discharge outlet.

* * * * *